United States Patent [19]

O'Donnell

[11] 4,081,366

[45] * Mar. 28, 1978

[54] PROCESS FOR DEWATERING ORGANIC WASTE PRODUCT

[75] Inventor: James M. O'Donnell, Woonsocket, R.I.

[73] Assignee: Orgonics, Inc., Slatersville, R.I.

[ * ] Notice: The portion of the term of this patent subsequent to Mar. 9, 1993, has been disclaimed.

[21] Appl. No.: 715,439

[22] Filed: Aug. 18, 1976

Related U.S. Application Data

[63] Continuation of Ser. No. 568,867, Apr. 17, 1975, Pat. No. 3,976,465, which is a continuation-in-part of Ser. No. 196,765, Nov. 8, 1971, abandoned.

[51] Int. Cl.$^2$ ............................................. C05F 3/00
[52] U.S. Cl. .......................................... 210/10; 210/18; 210/64; 210/65; 71/13; 71/16; 71/22; 71/25; 71/30; 71/64 E; 71/64 F; 426/69; 426/807
[58] Field of Search ................... 210/10, 18, 64, 65; 71/12, 13, 16, 21, 22, 24, 25, 28, 29, 30, 64 E, 64 F; 426/69, 807

[56] References Cited

U.S. PATENT DOCUMENTS

| | | | |
|---|---|---|---|
| 2,127,629 | 8/1938 | Jones | 71/16 |
| 3,073,693 | 1/1963 | Neilsson | 71/30 |
| 3,226,318 | 12/1965 | Schick | 71/13 |
| 3,227,543 | 1/1966 | O'Donnell | 71/28 |
| 3,279,979 | 10/1966 | Gribnau | 71/28 |
| 3,649,598 | 3/1972 | Namioka | 71/28 |
| 3,655,395 | 4/1972 | Karnematt | 71/28 |
| 3,705,794 | 12/1972 | Czwak et al. | 71/30 |
| 3,942,970 | 3/1976 | O'Donnell | 71/12 |
| 3,976,465 | 8/1976 | O'Donnell | 71/13 |

*Primary Examiner*—Charles N. Hart
*Assistant Examiner*—Ernest G. Therkorn
*Attorney, Agent, or Firm*—Richard P. Crowley

[57] ABSTRACT

A process for the chemical treatment of organic waste materials contaminated with a pathogenic microorganism, such as raw sewage, sewage sludge and other organic waste products, and to the treated organic waste material so obtained, which process comprises: prereacting the organic waste material with a water-soluble methylol compound subject to condensation, such as a methylolurea compound, under alkaline pH conditions; and, thereafter, condensing the methylol compound by establishing an acid pH condition to form a solid waste product comprising a condensation polymer containing methylene bridges and a sterile solid waste material.

18 Claims, No Drawings

PROCESS FOR DEWATERING ORGANIC WASTE PRODUCT

REFERENCE TO PRIOR APPLICATION

This is a continuation of application Ser. No. 568,867, filed Apr. 17, 1975, Pat. No. 3,976,465, which application is a continuation-in-part of Ser. No. 196,765, filed Nov. 8, 1971 (now abandoned).

BACKGROUND OF THE INVENTION

The disposal of waste products, such as human and animal digestive waste products, as well as the waste from industries, has always been a major social and economic problem. Such waste products include human and animal digestive waste products, and in addition, liquid waste products from industries, such as pulp and paper, meat slaughtering and packaging, cotton processing, canning, dairy products, sugar refining, frozen foods and vegetable, poultry, hides, leather and wool scouring and the like. Such industries produce waste products characterized by high biochemical oxygen demand levels and a large amount of suspended solids and pathogens. A variety of processes have been employed to render all of these pathogenic waste materials harmless, and to remove them as pollution factors. A great many of these processes employ a system of bacteriological decomposition.

Bacteriological decomposition processes often require enormous storage facilities because of the time required for bacteriological action, such as 30 to 60 days. In a typical process for the treatment of raw sewage, incoming raw sewage containing pathogenic microorganisms is sent through a comminutor where large solid material in the raw sewage is reduced in size, and then the sewage pumped to an aerated grit chamber where grit is removed. Such raw sewage contains less than 1% by weight of solids; for example, less than 2,000 parts per million of solid material. After removal of the grit, the sewage is directed to large settling tanks where the material is held for a period of time to permit settlement of the solids. Oleophilic material, such as grease, is then decantered from the surface of the liquid in the settling tanks, and the supernatant liquid removed from this primary settling tank and sent to a final aeration settling tank for a secondary treatment, and then further, forwarded to a chlorine-contact tank wherein typically about 99.8%, but less than all, of the pathogenic bacteria or microorganisms are killed by chlorine contact. The resulting liquid is then discharged into waterways or further chlorinated and recycled for reuse.

Typically, the raw sewage sludge removed from the primary treatment tank comprises from about 3 to 10% solids, which sludge is removed and sent to a digestion tank wherein the solids are decomposed by the reaction with a seeded bacteria which decomposes the carbohydrate waste material, generating heat and methane gas. The methane gas generated from such digestion tank(s) is often removed and used as fuel for heating the digestion tanks for other fuel purposes. Water is removed from the digestion tank from the decomposed solids, and, thereafter, the aerated or bacteria-digested raw sludge material is then formed into a cake-like material, either by the use of sludge beds or filters to form a moist cake product. The cake product, rich in nitrogen, may then be used for landfill, fertilizer, soil conditioner, or otherwise used or disposed of. Such a treatment process is commonly employed throughout the country to dispose of sewage products.

The decomposed solids or sewage sludge leaving the digestion tank and the supernatant liquid leaving the chlorine-contact tank often fall far short of being pathologically pure, or meeting the minimum standards required for effective pollution control. Numerous chemical methods are available for the further sterilization of these organic waste materials; however, cost and residual toxicity have rendered many of such techniques economically inadvisable.

There are a number of processes for the preparation of nitrogenous fertilizer compositions employing urea-formaldehyde condensates, such as, for example, those techniques described in U.S. Pat. Nos. 2,592,809; 2,644,806; 2,766,283; 2,830,036; 3,076,700; and 3,227,543. In addition, U.S. Pat. Nos. 3,073,693 and 3,226,318 are directed to the employment of polymerizable monomers with sewage solids to produce a synthetic nitrogen-containing fertilizer by-product.

For example, U.S. Pat. No. 3,073,693 prepares a nitrogenous fertilizer material by reacting sewage sludge, peat moss and a urea-formaldehyde solution, and immediately thereafter, condensing the urea-formaldehyde with the use of a strong acid to form a resin product. The reactants are admixed for between ½ and 2 minutes in an acid solution, whereby polymerization and condensation of the urea-formaldehyde is effected and the resulting mixture then admixed with an aqueous solution of ammonia to form the ammonium salt of the strong mineral acid. The sewage sludge employed is the type of sludge produced by the activation or digestant method; that is, an activated sterile sewage sludge, which has been removed from the digestion tank and dewatered.

U.S. Pat. No. 3,226,318 is directed to the consolidation by condensation of an aqueous waste sludge wherein a phenol-formaldehyde solution is added to the sludge, and promply thereafter, condensation is accomplished by the further addition of formaldehyde as a curing agent. This sewage treatment process is directed to a sewage sludge containing digested sewage solids and about 60% water in which a phenol-formaldehyde solution under acid conditions is condensed to provide a consolidated sludge product.

SUMMARY OF THE INVENTION

My invention comprises a new and improved process for the treatment of raw sewage, waste activated diluted sewage sludge, sewage sludge, and other solid organic-containing aqueous waste solutions, such as industrial organic waste material, to provide a solid waste. In particular, my invention concerns the process for treating organic waste material, such as raw sewage and sewage sludge, contaminated with a pathogenic microorganism and the sterile waste product produced. The process comprises reacting and sterilizing such solid waste material, and, thereafter, forming the solid waste material into a sterile, easily recoverable and usable waste product.

More particularly, my invention relates to a process for the treatment of raw sewage and waste activated or digested sewage sludge which contains pathogenic microorganisms. The process comprises: prereacting the waste material in the solution under alkaline pH conditions with a water-soluble, monomeric, condensable methylol compound to sterilize pathogenic organisms in the waste material; and, thereafter, condensing the monomeric methylol compound by establishing an acid pH condition in the solution to form a waste product which comprises a solid condensate having methylene bridges and solid sterilized organic waste material.

Even more particularly, my invention concerns the process for the treatment of liquid undecomposed raw sewage-containing organic solid waste material and contaminated with pathological microorganisms, which process comprises: prereacting and sterilizing the solution by adding thereto a urea-formaldehyde solution under alkaline pH conditions, which solution contains a water-soluble N-methylol monomeric material, and maintaining such materials in contact with the organic waste material for a sufficient period of time to sterilize said material; and, thereafter, condensing the urea-formaldehyde monomer by establishing an acidic pH condition to provide a solid pathologically sterile organic waste product.

In the preferred embodiment of my invention, nitrogen-containing monomeric compounds, such as mono and dimethylol urea (that is, the water-soluble reaction products of urea and formaldehyde) are prereacted under alkaline pH conditions with the organic waste material suspended in an aqueous solution. Raw sewage is typically acidic in nature and the solid material therein is hydrophilic. After prereacting and condensing, the solid organic waste product produced by my invention is hydrophobic in nature. I have found that my process permits the organic waste product to be easily dewatered and recovered in high yields from the aqueous solution. In addition, the use of urea-formaldehyde condensate provides for an inexpensive raw material and a linear-type, low molecular weight, short-chain polymer so that the resulting solid product of the process is easily broken up by a metabolic process when employed as an animal feed material, or by soil bacteria when employed as a fertilizer. The resulting waste product comprises a reacted admixture of a polyurea condensate and a pathogenically stable organic waste material, thereby providing a superior product for use as a metabolic process or for soil digestion.

In general, the monomeric methylol compounds in the solution are employed in an amount ranging from about 10 to 100% by weight of the organic waste material; for example, from about 50 to 80% of the organic waste material. However, it should be recognized that the amounts to be used may vary, depending upon the sterilizing or reacting effect desired and the amount of the condensate resin required to provide the proper ultimate end use of the product.

In my process, it is essential that effective sterilization of the pathologically containing organic waste material be achieved by contacting and reacting the waste material under alkaline pH conditions. Such contact and reaction should be with a methylol monomeric compound capable of further polymerization and/or condensation, and, in the preferred embodiment, for a sufficient period of time to effect the desired sterilization. Prior processes in which urea-formaldehyde or phenol-formaldehyde solutions have been incorporated into a sewage material have typically been for activated or digested sewage material and under acidic conditions to promote the rapid and effective condensation of the polymer to solid waste material. The waste material on which such techniques were employed comprised the digested or activated sewage sludge, rather than the raw sewage, or the unactivated sewage sludge from the settling tank.

My process is particularly advantageous in that effective sterilization and reaction of the waste material with a methylol monomer, such as an N-methylol monomer, converts the waste material into a solid product of a hydrophobic nature. The solid product produced by my process exhibits superior dewatering properties and produced by my process exhibits superior dewatering properties and permits recovery of the product at high yields. The condensation reaction with methylol-urea provides a nitrogen-containing waste by-product which may be employed as a slow nitrogen release fertilizer material. I have found that only very small quantities of a methylol-containing compound are sufficient to destroy the majority of the pathogens; for example, in generally less than thirty minutes. Further, in my process, any low solids waste material, such as sewage, may be treated; although in a preferred embodiment, sewage sludge prior to digesting is treated, thereby permitting the omission of the digesting step which requires large storage tanks, high capital investment and long time periods. Such treatment significantly reduces sewage odor in the process. If desired, my process may be effectively used on all types of pathogenic-containing waste materials, even digested sewage sludge, to effect even greater sterilization prior to consolidation and recovery of the solid product.

The solid pathogenically sterile organic waste product from my process, where such sewage material is not subjected to a bacterial decomposition or digesting step, is characterized by superior properties as a fertilizing or digestive material in that any breakdown of the long-chain carbohydrates in the material occurs when applied to the soil as a fertilizer or feed to animals. Thus, a novel, unique and improved fertilizer composition is prepared, which composition comprises an undigested pathogenically sterile solid sewage material containing a condensed or polymerized material having methylene bridges, particularly a condensed urea-formaldehyde, low molecular weight dimer or trimer condensate, which composition is particularly useful as a fertilizer in high-solid form, moist cake, or dry powder. Where desired, after treatment and recovery, the product may be concentrated and partially or fully dried and used in moist cake, powdered, granular, pellet or other form. The solid waste product of the process may also be directly employed as a fertilizer by spraying or otherwise applying the aqueous solution containing the product to a field or as an animal feed product. Other additives may be incorporated prior to condensation or thereafter, as desired, such as filler materials, additives to enhance color or taste, additives to aid in processing, such as flocculents, additives to aid in adjusting the ultimate use as a fertilizer, such as urea, other natural or synthetic fertilizers or compounds used in fertilizers, such as nitrogen-containing or phosphate compounds.

As used herein, the term "organic waste material" is intended to include raw sewage, solid sewage sludge recovered from municipal disposable units, as well as solid carbohydrate and proteinaceous material recovered from industrial waste liquors from the treatment of leather, wool, food, fish, meat products, dairy products, pharmaceutical waste products, such as antibiotics, and the waste products of bio-organic materials and the like, which organic waste materials typically contain pathogenic microorganisms. In a preferred embodiment of my invention, such organic waste materials would include raw sewage and waste activated sewage sludge; that is, prior to digestive techniques. However, where desired, my process may also be usefully employed in reacting varied or digested sewage sludge or other materials which have been treated to remove substantially all or a portion of the pathogenic microorganisms therein.

I have found that effective sterilization of organic waste materials can be accomplished in one embodiment by incorporating and reacting a solution of urea and formaldehyde under alkaline pH conditions into and with said organic waste material. The urea and formaldehyde typically have a urea-formaldehyde mole ratio of greater than 1:1; for example, 1:1 to 2:1, but preferably in a range of 1.3:1 to 1.8:1, whereby the urea is in excess of the formaldehyde to be employed. Under such conditions, urea-formaldehyde reacts to form the mono or dimethylol urea or mixtures thereof. The water-soluble N-methylol-containing monomer, when held in contact and reacted under suitable time and temperature conditions with the waste material, effectively prereacts with and sterilizes the waste material. An excess of urea is preferred, but not necessary if a cross-linked condensate is acceptable in the resulting waste product. The use of excess urea provides for a linear, rather than cross-linked, polymer.

I have found that surprising results in dewatering properties and solids recovery are obtained, as well as economic benefits, if the urea and formaldehyde are prereacted to form the methylol compound under alkaline conditions, and the methylol compound is added to the aqueous solution containing the organic waste material, rather than the separate use or addition of the urea and formaldehyde and an insitu reaction. Further, I have discovered that prereacting the urea and formaldehyde just prior to use, rather than the employment of an aged urea-formaldehyde solution, is desirable. The urea-formaldehyde is reacted under alkaline conditions until a proper degree of methylolization is achieved. Urea in either crystalline, prilled, solution or other form is added to the formaldehyde in the presence of water and a suitable buffering agent to maintain an alkaline pH of, for example, between about 7.0 to about 9.0, thereby forming the water-soluble mono and/or dimethylolurea monomer.

The concentration of urea and formaldehyde will depend largely upon the physical conditions of the organic waste material being used. In general, the most effective method is to dissolve either crystalline or prilled urea in a 37% aqueous solution of formaldehyde which has been buffered, then diluting this preparation accordingly to meet the requirements of the organic waste material to be sterilized. The waste material to be reacted with the methylol compounds should be in a fluid or semifluid sludge state in order to allow permeation of the methylol solution into reactive contact with the particulate solid material.

My invention will be described in particular concerning the use of urea-formaldehyde concentrates; however, it is recognized that other aldehydic compounds may be employed in place of the formaldehyde solution, such as the use of paraformaldehyde, crotenaldehyde, acetaldehyde, propionaldehyde, furfural, and the like in order to prepare a methylol monomer. Urea-formaldehyde is the preferred alkaline monomeric solution, since such material is a low-cost nitrogen-containing material which provides for N-methylol groupings, and, further, the nitrogen of the urea is effective in providing a slow-nitrogen-releasing fertilizing composition.

In determining the particular concentration of the methylol monomer to be employed, consideration should be given to any side reactions which might react with the methylol compound in the organic waste material, such as ammonia, sodium bisulfide and the like. The concentration to be employed in my process may vary, depending upon the ultimate end use of the solid waste product. For example, if the product is to be employed merely as a sanitary landfill or as fuel where there is little or no recovery of cost of treatment, only minimal concentrations sufficient to obtain the desired sterile levels; e.g., to prevent odors or to improve the dewatering properties, should be employed. However, if the product is to be employed as a fertilizer or as an animal feed supplement, then larger concentrations are often advantageous, since the cost can be recovered and the high nitrogen content resulting from the treatment lowers the transportation cost of the product to its point of distribution. It is theoretically possible to reach a concentration which results in a waste product with a nitrogen content of about 38% by weight. However, the concentration of the organic waste material would be so low as to be relatively ineffective as a useful product.

It is essential that the reaction time and concentration of the methylol-containing monomeric solution with the organic waste material under alkaline pH conditions be sufficient to insure the desired reaction and/or sterilization. The contact time is dependent largely upon the temperature of the resulting organic waste slurry and the presence of other bactericidal catalytic agents, such as soaps, synthetic detergents, alcohol, and the like which may have an affect on the bactericidal and reaction activity of the methylol monomeric materials. Typically, complete sterilization of an organic waste material at a temperature of 5° to 10° C requires a contact time of up to 3 to 4 hours, while, at a temperature of 20° C, only about 5 to 30 minutes is required. At temperatures of 60° C and more, the reaction and sterilization appear to take place very rapidly in a matter of 1 to 10 seconds with methylol-urea. A preferred contact and reaction time employing a urea-formaldehyde-methylol monomeric solution is between about 5 minutes and 2 hours at temperatures of between about 20° C and 60° C.

In the preferred embodiment, a methylol-urea monomer solution is incorporated into an organic solid waste product sludge containing a pathogenic microorganism under alkaline pH conditions. Furthermore, the solution may be incorporated directly into raw sewage; that is, undigested sewage; e.g., having about 5 to 50% by weight of solid material. The methylol monomers employed should be water-soluble monomers or mixtures of water-soluble monomers subject to the further condensation and/or polymerization.

After reaction and sterilization of the organic waste material, the methylol compound is subject to a condensation or polymerization reaction, which converts the highly toxic methylol groups of the mono or dimethylol-urea to nontoxic methylene bridges in the condensate polymer. One method of accomplishing condensation of urea-formaldehyde solution wherein urea is in the excess is to reduce the pH of the alkaline reaction solution to the acid side; for example, to between 2.0 and 5.0, by the addition of a suitable organic or inorganic acid. The time for condensation is effected by the temperature and pH conditions. For example, when employing a urea-formaldehyde solution, a reduction of the pH to about 5.0 and the employment of a temperature of about 15° C, complete methyleneization or condensation often requires about 2 days. However, when the temperature is increased to 80° C, the condensation reaction is often completed in as little as 2 to 10 minutes. I prefer to employ a pH of approximately 3.0 to 4.5 at a temperature of between 60° and 80° C which effects condensation in a period of time between 1 and 20 minutes, such as, for example, 1 to 5 minutes.

Where desired, other monomers or polymerizable monomers or polymers may be incorporated into the organic waste material and condensed or interpolymerized with the methylol compounds. For example, the urea-formaldehyde solution wherein the formaldehyde ratio is from 1 to 5 moles per mole of urea may be employed to effect reaction and sterilization of the organic waste material, and then subsequently urea added separately so that the urea is in excess, and then the resulting urea-formaldehyde solution condensed by reducing the pH by the addition of an acid. Any acid or acid salt may be employed to reduce the pH; for example and preferred are inorganic acids, such as sulfuric acid, sulfonic acid, hydrochloric acid and phosphoric acid.

Depending upon the ultimate use of the waste product, the pathologically sterile treated waste product from my process may be disposed of as a pathologically pure organic waste material. However, if the waste product is to be recycled into the food chain as a fertilizer or animal feed or animal feed supplement, then typically it should be further treated, such as by neutralization, or otherwise properly prepared for acceptance in the marketplace. Where the product is to be useful as a fertilizer and animal feed supplement, the product should contain a low molecular weight linear condensate therein; that is, where the molecular weight, for example, ranges from 120 to 250, such as below 800, or where the urea-formaldehyde condensate is primarily methylene diurea or trimethylene tetraurea, or the like. For such use, the condensate should be generally straight-chain, branch or graft-type condensates which may be easily broken down by the nitrogen-acting bacteria of the soil, or by the metabolic process in the digestive tract of the animal. The resulting condensate or polymer should not be a highly cross-linked complex resin, but rather a low molecular weight dimer, trimer and tetramer.

A neutralization step may be employed in order to stabilize the methylene urea-formaldehyde condensate which might otherwise tend to form highly cross-linked condensates, rather than the straight-chain, branch or graft-type condensates which are sought in my process. The neutralization step may be accomplished by the addition of a suitable organic or inorganic base to the waste product in the solution. For the purposes of economy and availability, I prefer the employment of hydrated lime, ammonia, ammonium salts of calcium carbonate as the neutralizing agent. After neutralization or where the product is not to be neutralized, the waste product may be prepared in a suitably accepted dry or granular form by subjecting the material to a drying step, such as by spray-drying or the like, at which point the material is ready for packaging and distribution or disposal.

The resulting waste product or my process comprises the condensed methylol polymer preferably in low molecular weight linear form, and the reacted sterilized organic waste material which, by the reaction and sterilization under alkaline conditions, is converted from a hydrophilic state to a hydrophobic state. The waste product by such reaction and sterilization is characterized by superior and improved properties of dewatering or filterability so that a high solids content is obtained on filtering or other recovery steps or processes. The suspended waste product may be directly used in slurry form, such as by spraying as a fertilizer onto crops or fields, or directly disposed of as refuse.

In the preferred embodiment, the hydrophobic suspended particles of the sterilized waste product are recovered from the aqueous solution, such as through the employment of filters or other recovery means like centrifuging, gravity filtering, etc. The improved dewatering properties of the waste product permit high solids recovery of the product from the slurry solution.

For the purposes of illustration only, my invention will be described through the employment of a urea-formaldehyde solution with organic waste material.

DESCRIPTION OF THE PREFERRED EMBODIMENTS

Example 1

A sample of raw undecomposed; i.e., unactivated, sewage sludge was obtained from the sewage treatment plant located at the City of Woonsocket, R.I. Analysis of the material showed the following:

| | |
|---|---|
| Total solids | 6% |
| Total Nitrogen (solids) | 2% |
| Bacteriological Report | |
| Culture report indicates the pressure of | |
|     Streptococcus (alpha) Gr. 0 | |
|     Escherichia coli | |
|     Enterobacter Group | |
|     B. Sablilis | |
|     Smear Report: | |
|       -Gram neg. - gram pos. rods | |
|       gram positive diplorocci | |

1,000 grams of this raw sewage sludge was treated with 60 grams of a urea-formaldehyde solution prepared in the following manner:

50 grams of commercially available 37% formaldehyde was neutralized with triethanolamine to a pH of 8.0. To this was added 50 grams of a commercially available prilled urea containing 46% nitrogen. The negative heat of solution caused a drop in temperature to 5° C. The solution was gently heated to 30° C at which point the urea was in solution with the formaldehyde. After 10 minutes the temperature of this solution rose to 60° C at which point it was added to the 1,000 grams of sewage sludge.

The resulting mixture (a heavy viscous mass) was kept under constant agitation at a temperature of 20° to 25° C. The temperature was raised to 60° C and maintained at this level for a period of about 30 minutes at which time sufficient dilute hydrochloric acid was added to reduce the pH to 3.0.

The resulting slurry began to thicken quite rapidly at this point and was transferred to a mechanical kneader for further handling. After a period of about 5 minutes, the methyleneization was considered complete because of an absence of any formaldehyde odor.

The compound was further tested by Deniges method and a modified Schiff's reagent and no formaldehyde was found to be present.

At this point a sufficient quantity of calcium carbonate was added to neutralize the mixture and to raise the pH to 6.5 to 7.0.

Without further treatment, the product was subjected to the same analysis as the raw sewage sludge with the following results:

| | |
|---|---|
| Total solids | 10% |
| Total Nitrogen (solids) | 21% |
| Bacteriological Report | |
| Culture — no growth | |
| Smear — no bacteria | |

A portion of the above sample was passed through a 10-mesh sieve. The resulting granular product was then subjected to drying at 100° C for a period of 30 minutes. The sample was then analyzed for its agronomic usefullness as a high analysis organic nitrogen fertilizer.

The qualities sought for in an organic material as a fertilizer are:

I. NITROGEN PLANT FOOD CONTENT

Most nitrogenous organic fertilizers contain about 6% nitrogen, while the average mineral or inorganic fertilizer contains between 10 and 20 percent of this essential plant food element. From the economic standpoint of transportation and application of fertilizer this means that the currently available sources of organic fertilizers are between 100 and 300 percent more expensive than their mineral counterparts. Therefore, an organic compound with competitive nitrogen contents would be highly desirous.

II. INSOLUBLE NITROGEN CONTENT

Organic forms of nitrogen have always commanded a premium price in the fertilizer market because of the relative insolubility of their plant food nitrogen. This insolubility leads to longer lasting nitrogen and considerably less leaching of the nitrogen. From the standpoint of ecology, insoluble forms of nitrogen prevent leaching or washing into surrounding water stratums, rivers, streams, etc.. Insoluble forms of nitrogen usually depend on their release of nitrogen plant food through natural bacterial decomposition in the soil. This results in a more gradual release of the nitrogen plant food, as well as a stimulation of the soil micro flora and fauna.

III. QUALITY OF INSOLUBLE NITROGEN

Many forms of insoluble nitrogen are so tightly bound in complex molecules that for all practical purposes they are available for bacterial breakdown and therefore cannot enter the food chain cycle. Recent work has indicated that the availability of insoluble nitrogen can be obtained by determining the percentage of water insoluble nitrogen which dissolves when a sample of 0.25 grams of the product is heated to 100° C for 30 minutes in 250 milliliters of neutralized water. The percentage figure thus obtained is called the "Activity Index". It is generally accepted that a product with an "Activity Index" of greater than 40 will yield the bulk of its nitrogen within a six-months incubation period in the soil. The analysis of the product obtained from this example was:

| | |
|---|---|
| Total Nitrogen | 21% |
| Insoluble Nitrogen | 15% |
| Activity Index | 55 |

EXAMPLE 2

1,000 grams of a fish meal intended for use as a poultry feed supplement, and containing about 9% nitrogen, and found to be contaminated with pathogenic salmonella was treated with 10, 20, 30, 40, 50, 60, 70, 80, 90, and 100 grams respectively of a urea-formaldehyde solution prepared in the same manner as indicated in Example 1.

The urea-formaldehyde solution was added to the dry fish meal as a fine spray, while the meal was being rotated in a cylinder similar in appearance to a small sized cement mixer.

The temperatures of the resulting mixtures were raised to 30° C. The products were held at this temperature for a period of about 2 minutes at which point the methyleneization step was introduced by spraying a dilute solution of hydrochloric acid until a pH of 3.0 was recorded. The products were held under this condition until methyleneization was complete as indicated by the tests performed in Example 1. A sufficient amount of calcium carbonate was added to the mixtures to insure a neutral pH.

Without further treatment, the samples were subjected to bacteriological and chemical analysis with the following results:

| | | Salmonella | %Protein |
|---|---|---|---|
| Check | 0 treatment | + | 56.25 |
| | 10 gr. treatment | − | 57.09 |
| | 20 gr. treatment | − | 57.93 |
| | 30 gr. treatment | − | 58.78 |
| | 40 gr. treatment | − | 59.62 |
| | 50 gr. treatment | − | 60.46 |
| | 60 gr. treatment | − | 61.30 |
| | 70 gr. treatment | − | 62.14 |
| | 80 gr. treatment | − | 62.98 |
| | 90 gr. treatment | − | 63.82 |
| | 100 gr. treatment | − | 64.66 |

EXAMPLE 3

A sample of tannery waste sludge containing about 10% solids and composed of such materials as fleshings, hair, entrails, and general nide scrappings (in addition to these organic constituents there was a sufficient amount of sulfide contamination to cause considerable odor problems) was subjected to our treatment by adding 166 grs. of urea-formaldehyde solution, prepared in accordance with Example 1, to 1,000 grams of the tannery waste sludge.

In the same manner as previously disclosed, the resulting slurry was maintained at a pH of 8.0 and a temperature of 30° C for a period of 30 minutes.

The pH was then reduced to 3.0 by the addition of a dilute solution of sulfuric acid and the temperature was raised to 60° C. Sufficient agitation was supplied to maintain a state of equilibrium between solid and liquid phases. Methyleneization was allowed to continue to a point where no free formaldehyde was detected by Deniges method described in Example 1.

The resulting mixture was then neutralized with a sufficient quantity of a dilute sodium hydroxide solution (1% NaOH) to raise the pH level to 7.5, dried by subjecting the mixture to a continuous stream of hot air (110° C) while tumbling in a rotating cylinder for a time sufficient to reduce the moisture content to about 5% and then ground to a uniform particle size (-10-20 mesh).

This product was then analyzed for its agronomic properties and found to contain the following:

| Total Nitrogen | 24.2% |
|---|---|
| Insoluble Nitrogen | 19.0% |
| Activity Index | 52.0 |

The process of my present invention has many advantages in the treatment of pathogenic waste materials in so far as the investment of capital equipment is minimal. For example, a small jacketed reaction vessel may be used to prepare the methylol solution. This solution may be added batch-wise or continuously to the organic waste material. The methyleneization step of our process can be carried out by an in-line injection of the mineral or organic acid. Neutralization can also be effected in the same manner. Both steps can be greatly accelerated by elevating the temperature of the organic waste material to be treated. In the case of a sludge-like material such as the raw sewage sludge and tannery waste used in our experiments, the material can be passed through a heat exchange. The urea-formaldehyde solution can also be handled in the same manner. In the case of dry materials, such as the fish meal used in our second experiment, they can be passed through a rotating cylinder concurrently or countercurrently to a stream of heated air in order to raise the temperature to around 60° C.

EXAMPLE 4

It has been found that the preparation of a preformed urea-methylol solution and prereaction with an organic waste material provides unexpected and increased efficiency in the dewatering of the waste product from the solution. The addition and prereaction of the methylol solution is superior to the addition separately of urea or formaldehyde and in situ condensation.

Two buckets of sewage sludge were collected from the Merrimack, New Hampshire waste treatment plant. In each run, 1,000 ml of sludge were used. Adjustment of pH in the process was done with 12% KOH for the alkaline step, and 30% $H_3PO_4$ for the acid step. Both samples of sludge contained 3.7–4.0% solids as determined by overnight drying at 100° C. The samples were treated with urea, formaldehyde and urea-formaldehyde methylol solutions as set forth in Table I.

TABLE I

| Sample No. | Ml Sludge Taken | Reactant Added | Reactant-to-Sludge Solids ratio | Grams Urea Grams Formaldehyde |
|---|---|---|---|---|
| 1 | 1,000 | U/F | 1/1 | 20/20 |
| 2 | 1,000 | U/F | 1.5/1 | 30/30 |
| 3 | 500 | Blank | — | — |
| 4 | 1,000 | U-F | 1/1 | 20/20 |
| 5 | 1,000 | F-U | 1/1 | 20/20 |
| 6 | 1,000 | F-U | 1.5/1 | 30/30 |
| 7 | 1,000 | U-F | 1.5/1 | 30/30 |
| 8 | 1,000 | U/F | 1.5/1 | 30/30 |

*U/F = Normal makeup of urea-formaldehyde solution (methylol solution)
U-F = Urea added for 10 minutes followed by formaldehyde for 10 minutes
F-U = Formaldehyde added first, followed by urea - same time.

All samples were treated at 60°–65° C at pH 7.2 to 7.5 alkaline conditions, and then subsequently converted to an acid condition pH of 3.0 to 3.5. The samples were placed in one quart plastic containers and filtered.

Filtrations were carried out, of 200 grams of each sample, through two pieces of 12.5 cm Whatman #1 filter paper using a vacuum pump set at 15 inches water vacuum. The amount of filtrate obtained in 10 minutes was determined along with the grams and percent solids of the filter cake.

Sedimentation tests were attempted in 40 ml centrifuge tubes; however, because of the heavy amount of flocculation, sedimentation rates had to be carried out on diluted samples (35 gram sample — 15 grams water) and thoroughly shaken before sedimentation.

Table II shows the results of the filtration experiment. The processed sludge samples, regardless of the method, filtered well, while the blank sample filtered only slightly in the 10-minute period. In comparing the (F-U) versus the (U-F) method, the (F-U) gave better filtrations. The U/F preparation gave the highest solids filter cake at both reactant levels of 1/1 and 1.5/1.

TABLE II

| Sample No. | Reactant Added | React/Sludge Ratio (GMS) | ML* Filtrate | GMS** Filter Cake | % Solids Filter Cake |
|---|---|---|---|---|---|
| 1 | U/F | 1/1 | 157 | 40.8 | 21.2 |
| 2 | U/F | 1.5/1 | — | — | — |
| 3 | Blank | — | 35 | Too wet to determine | |
| 4 | U/F | 1/1 | 134 | 58.9 | 14.7 |
| 5 | F-U | 1/1 | 151 | 45.9 | 18.5 |
| 6 | F-U | 1.5/1 | 151 | 47.4 | 23.7 |
| 7 | U-F | 1.5/1 | 145 | 52.0 | 19.4 |
| 8 | U/F | 1.5/1 | 151 | 47.8 | 25.5 |

*After 10 minutes filtration at 15" vacuum
**Grams wet filter cake after 10 minutes The sedimentation tests showed only that all the processed samples, regardless of the method, settled out in a uniform rate; that is, no differences in sedimentation rate were seen. After one hour in the centrifuge tubes, samples 1, 6, 7 and 8 showed 6 ml of clearing. The blank showed only 1 ml, indicating that processing did have an affect on the sedimentation.

The use of methylol solution (sample #1) in comparison to the addition of formaldehyde first (sample #5) provided for an additional 2.7% solids collection or an increased dewatering efficiency of 14.5%. Sample #8 compared with sample #7 with urea added first provided for an additional 6.1% solids on increase in efficiency of 31.4%.

My process has also the advantage that it can reduce organic waste materials to pathologically pure materials which can be recycled to the ecology in a matter of minutes, where as concurrently available methods require 30 to 60 days to achieve a similar result.

This process has further advantages in that its products can be recycled to the ecology at a level substantially higher than similarly biologically treated products. Biologically treated products are not pathologically pure and therefore cannot be considered for use as an animal or human feed supplement. The products of my invention are pathologically pure and could be considered for these purposes.

What I claim is:

1. A process for dewatering a solid reaction material from an aqueous solution, containing organic waste material which process comprises:
   a. prereacting an aqueous solution of urea and formaldehyde under alkaline conditions, the urea-formaldehyde having a mole ratio of greater than 1:1 to provide an aqueous urea-formaldehyde solution which comprises a mixture of water-soluble mono and dimethylol urea monomers and an excess of urea;

b. adding the prereacted urea-formaldehyde solution to an aqueous solution containing solid organic waste material;

c. reacting the mono and dimethylol urea monomers with the organic waste material while maintaining the pH of the reaction solution from about 7.0 to 9.0;

d. condensing the mono and dimethylol ureas in the alkaline reaction solution by adding an acid or acid salt to establish an acid pH condition of from about 2.0 to 5.0 in the reaction solution to form a sterile solid water-insoluble reaction product which comprises a reaction admixture of an essentially linear solid polyurea condensate having methylene bridges, and a molecular weight of less than 800 and solid organic waste material; and e. dewatering and recovering the solid reaction product from the solution.

2. The process of claim 1 which includes recovering the solid reaction waste product from the solution by filtering the reaction waste product from the solution.

3. The process of claim 1 wherein the urea-formaldehyde mole ratio is from 1.3:1 to 1.8:1.

4. The process of claim 1 wherein the solid organic waste material comprises raw, undecomposed sewage having a solid content of about 5% to 50% by weight.

5. The proces of claim 1 wherein the solid organic waste material comprises an undigested sewage material.

6. The process of claim 1 wherein the solid organic waste material comprises a fishmeal waste product.

7. The process of claim 1 wherein the solid organic waste material comprises a tannery waste sludge.

8. The process of claim 1 wherein the alkaline pH condition comprises a pH of from about 7.0 to 8.0, and the acid pH condition comprises a pH of from about 3.0 to 4.5.

9. The process of claim 1 which includes the step of neutralizing the acidic solution containing the solid product by the addition of a base prior to dewatering the solid reaction product.

10. The process of claim 9 which includes neutralizing the solution by adding thereto hydrated lime, calcium carbonate or ammonia.

11. The process of claim 1 wherein the acid pH conditions are established by adding to the solution containing the prereacted organic waste material sulfuric acid, hydrochloric acid, phosphoric acid or the acid salts thereof.

12. The process of claim 1 which includes carrying out the condensing step at a temperature ranging from about 10° to 80° C and from a period of time from about 2 minutes to 2 days.

13. The process of claim 1 wherein the aqueous solution containing the solid organic waste material is acidic, which process includes adding to the solution an alkaline material in sufficient quantities to form the desired pH condition prior to adding the urea-formaldehyde solution.

14. The process of claim 1 wherein the solid condensate is an essentially linear, low-molecular-weight, short-chain dimer, trimer and tetramer urea condensate having a molecular weight of less than about 800, the condensate subject to being broken up by metabolical or bacterial processes.

15. The process of claim 1 wherein the water-soluble monomeric methylol ureas are present in an amount of from about 10 to 100% of the organic waste material in the solution.

16. The process of claim 1 wherein carrying out the reaction step is carried out at a temperature of about 20° to 60° C for a time of 5 minutes to 2 hours.

17. The process of claim 1 wherein the dewatering is carried out by vacuum filtration of the reaction product from the solution.

18. A process for dewatering a solid reaction material derived from a sewage sludge, which process comprises:

a. prereacting a urea-formaldehyde solution to form an aqueous solution under alkaline pH conditions of water-soluble, monomeric mono and dimethylol ureas and an excess of urea;

b. adding the prereacted urea-formaldehyde solution to undigested or waste-activated sewage sludge material in an aqueous solution, and reacting the waste material in the solution under alkaline pH conditions of from about 7.0 to 9.0 with the water-soluble, monomeric, methylol ureas in the presence of the excess of urea;

c. thereafter condensing the methylol ureas by adding an inorganic acid or acid salt to establish an acid pH condition of from about 3.0 to 5.0 in the solution, and to form a solid, water-insoluble reaction product, which product comprises a solid polyurea condensate having methylene bridges, a molecular weight of less than 800 and composed essentially of a linear-type, low-molecular-weight condensate and solid organic waste material;

d. adding an alkaline material to the solution containing the solid product and in an amount sufficient to neutralize the solution containing the solid product; and, thereafter, e. filtering the solid reaction product from the solution and recovering a solid reaction product.

* * * * *